United States Patent
Aamodt et al.

(10) Patent No.: US 10,003,063 B2
(45) Date of Patent: Jun. 19, 2018

(54) BATTERY ASSEMBLY FOR IMPLANTABLE MEDICAL DEVICE

(71) Applicant: Medtronic, Inc., Minneapolis, MN (US)

(72) Inventors: Paul B. Aamodt, Minnetonka, MN (US); Bernard F. Heller, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 15 days.

(21) Appl. No.: 14/692,770

(22) Filed: Apr. 22, 2015

(65) Prior Publication Data
US 2016/0315302 A1     Oct. 27, 2016

(51) Int. Cl.
 *H01M 2/20* (2006.01)
 *A61N 1/375* (2006.01)
 *A61N 1/378* (2006.01)

(52) U.S. Cl.
 CPC .......... *H01M 2/204* (2013.01); *A61N 1/378* (2013.01); *A61N 1/3752* (2013.01); *A61N 1/3754* (2013.01); *A61N 1/3756* (2013.01)

(58) Field of Classification Search
 CPC ........ H01M 2/06; H01M 2/204; H01M 2/202; A61N 1/36; A61N 1/362
 See application file for complete search history.

(56) References Cited

U.S. PATENT DOCUMENTS

| | | |
|---|---|---|
| 6,746,798 B1 | 6/2004 | Hiratsuka et al. |
| 6,844,106 B2 | 1/2005 | Heller, Jr. |
| 7,260,434 B1 | 8/2007 | Lim et al. |
| 7,337,002 B2 | 2/2008 | Gramse et al. |
| 7,556,298 B2 | 7/2009 | Viavattine et al. |
| 7,736,191 B1 | 6/2010 | Sochor |
| 8,003,248 B2 | 8/2011 | Freitag et al. |
| 8,206,180 B1 | 6/2012 | Kast et al. |
| 8,267,708 B1 | 9/2012 | Sochor |
| 8,433,409 B2 | 4/2013 | Johnson et al. |
| 8,700,160 B2 | 4/2014 | Troosters et al. |
| 2006/0096082 A1 | 5/2006 | Aamodt et al. |
| 2006/0099496 A1 | 5/2006 | Aamodt et al. |
| 2007/0150020 A1* | 6/2007 | Hokanson ............ A61N 1/378 607/30 |
| 2010/0256695 A1 | 10/2010 | Iyer et al. |
| 2012/0107669 A1 | 5/2012 | Viavattine |
| 2013/0302665 A1 | 11/2013 | Zhao et al. |

OTHER PUBLICATIONS (PCT/US2016/028570) PCT Notification of Transmittal of the International Search Report and the Written Opinion of the International Searching Authority, or the Declaration, dated Jun. 17, 2016, 5 pages.

* cited by examiner

*Primary Examiner* — Raymond Alejandro (57) ABSTRACT

A battery assembly comprises a battery housing that defines an opening and includes one of a first engagement member and a second engagement member. A feedthrough member is disposed with the opening and extends from the battery housing. A connector includes at least one electrical terminal electrically communicating with the feedthrough member and includes one of a first engagement member and a second engagement member. The engagement members are disposable in a mating configuration to assemble the battery housing and the connector. Implantable medical devices, systems and methods are disclosed.

20 Claims, 9 Drawing Sheets

BATTERY ASSEMBLY FOR IMPLANTABLE MEDICAL DEVICE

TECHNICAL FIELD

The present disclosure generally relates to electrochemical power cells and battery assemblies incorporating such power cells and more particularly to electrochemical cell encasements including covers, cases, and connectors for the electrochemical cells used to power implantable medical devices.

BACKGROUND

Electrochemical cells in the form of batteries are conventionally used to power many types of electronic devices, and are available in several forms, including, for example, cylindrical, button, pouch and prismatic cells. In some cases, electrochemical cells and methods of making cells for use in an implantable medical device (IMD) can be designed in a compact configuration, such that an IMD can be readily implanted in small spaces within a patient's anatomy. As such IMDs are required to be smaller for various medical applications, new challenges in manufacturing of the components for the IMDs, such as batteries, present themselves. One such IMD is a pacemaker. In one example, a leadless pacemaker can be implanted directly within the heart, attached to an interior wall of a heart chamber, and incorporate both a battery and electronics for providing stimulus to the heart. Such an IMD eliminates the need for leads used in conjunction with conventional pacemakers, which typically run from a pacemaker implanted external to the heart to positions within heart.

To provide a pacemaker that can be implanted within a heart chamber, the size of the pacemaker is reduced to a volume that can not only fit inside the heart chamber, but which is sufficiently small so as not to significantly interfere with the heart operations in terms of expansion and contraction, and blood flow through the heart. Still further, the pacemaker should be capable of operation over a period years such that the battery provides sufficient energy storage for such operation yet remain within the size constraints dictated by intra-heart operation.

In one example, battery energy storage is directly related to the volume of the anode and cathode electrodes, which react via an electrolyte fluid. Aside from improvements in electrochemical cell materials that could provide greater energy density, the size of the battery is typically dictated by energy requirements with the remaining volume dictated by packaging requirements. As such, packaging requirements for such an IMD can be stringent and include proper sealing over a lifetime of such a battery.

One exemplary consideration of such IMDs is size requirements, which can include the size of a feedthrough conductor that can be reduced resulting in a conductor that is delicate and connected to IMD components with care. This design can be employed to avoid excessive displacement of the conductor, which can lead to electrical shorting. Accordingly, error tolerances in making connections to such a feedthrough conductor of the battery are commensurately stringent and may require multiple tooling operations to make such connections. This disclosure describes an improvement over these prior technologies.

SUMMARY

In one embodiment, a battery assembly is provided. The battery assembly comprises a battery housing that defines an opening and includes one of a first engagement member and a second engagement member. A feedthrough member is disposed with the opening and extends from the battery housing. A connector includes at least one electrical terminal electrically communicating with the feedthrough member and includes one of a first engagement member and a second engagement member. The engagement members are disposable in a mating configuration to assemble the battery housing and the connector. In some embodiments, implantable medical devices, systems and methods are provided.

BRIEF DESCRIPTION OF THE DRAWINGS

FIG. 3a is break away perspective view of components shown in FIG. 2a;

FIG. 3c is break away perspective view of components shown in FIG. 2a;

FIG. 3d is a plan view of the components shown in FIG. 2a, in part cross section, taken along line 111c-111c of FIG. 3a;

FIG. 3e is a plan view of components shown in FIG. 2a;

FIG. 4b is a plan view of the components shown in FIG. 4a;

FIG. 4c is a side view of the components shown in FIG. 4a;

FIG. 4d is a side view of the components shown in FIG. 4a;

FIG. 4e is a side view of the components shown in FIG. 4a;

FIG. 4f is a side view of the components shown in FIG. 4a;

FIG. 6 is an enlarged detail view of mating engagement of components shown in FIG. 2a;

DETAILED DESCRIPTION

The exemplary embodiments of electrochemical power cells and battery assemblies disclosed are discussed in terms of medical devices for therapeutic treatment of a subject, and more particularly to electrochemical cell encasements including covers, cases, and connectors for the electrochemical cells used to power implantable medical devices. In some embodiments, a battery assembly is provided that includes positioning features. In some embodiments, the battery assembly is employed with a method for positioning an electronic component on a battery of an implantable medical device such that connection of the component with the battery is tightly toleranced.

In some embodiments, the battery assembly includes positional features added to components of an implantable medical device, which may include electronic components and/or the battery assembly, to provide alignment for connection of implantable medical device components during assembly. In some embodiments, the positional features allow the implantable medical device components to connect and/or mate in an interference fit, friction fit, pressure fit and/or press fit that provides locking of the components. In some embodiments, the positional features include locking elements that insure that the implantable medical device components are assembled and held in place where desired. In some embodiments, the positional features limit the ability for the implantable medical device components to rotate, and/or move in one or a plurality of axial directions, such as, for example, translation in x, y or z directions. In some embodiments, the positional features provide structural assistance to weld connections used to hold a connector in place with a battery by preventing rotational movement or flexing while in use.

In some embodiments, the battery assembly is employed with a method for assembly of implantable medical device components that allows for less fall-out at an inspection for position, as well as avoiding excessive tooling requirements for assembly. In some embodiments, the battery assembly includes positional features that allow placement of implantable medical device components in positional alignment without requiring placement via tooling.

In some embodiments, the battery assembly comprises a battery housing and a connector arrangement, which provides for precise alignment of a conductor of a battery with a connector and the attachment of the connector to the battery housing. In some embodiments, this battery assembly configuration provides an assembly arrangement for effecting connections from a feedthrough conductor of the battery to IMD electronics. This configuration can provide for precise alignment of a connector with a battery feedthrough conductor to permit powering of the electronics without misalignment of the connector and resultant displacement of the feedthrough conductor.

In some embodiments, the battery assembly comprises a battery housing defining a feedthrough aperture and a housing including an electrochemical battery assembly configured to produce an electrical potential. In some embodiments, a feedthrough member electrically communicates the electrochemical battery assembly to outside the battery housing by passing through the feedthrough aperture to extend above an exterior surface of the battery housing. In some embodiments, a connector body includes at least one electrical terminal electrically communicated to the feedthrough member, such as, for example, a feedthrough pin. In some embodiments, the connector body has a first engagement member, and the exterior surface has a second engagement member configured to mate with the first engagement member in an interference fit, friction fit, pressure fit and/or press fit engagement.

In some embodiments, the battery assembly comprises a battery housing defining a feedthrough aperture and housing including an electrochemical battery assembly configured to produce an electrical potential. In some embodiments, the battery assembly comprises a feedthrough member, optionally formed as a pin, which electrically communicates the electrochemical battery assembly to outside the battery housing by passing through the feedthrough aperture. In some embodiments, the battery assembly comprises a connector body that includes at least one electrical terminal electrically communicated to the feedthrough pin and the connector body has one of a first engagement member and a second engagement member. In some embodiments, the battery assembly comprises an exterior surface of the battery that has another one of the first and second engagement members configured to mate with the first engagement member in an interference fit, friction fit, pressure fit and/or press fit engagement.

In some embodiments, the first engagement member includes at least one rib, and the second engagement member includes at least one slot configured to accept the at least one rib in an interference fit, friction fit, pressure fit and/or press fit. In some embodiments, the engagement member includes at least one rib including a first rib and a second rib, and the at least one slot includes a first slot and a second slot. In some embodiments, the engagement member includes first and second ribs arranged at an angle with respect to one another and first and second slots arranged at an angle with respect to one another. In some embodiments, the angle is 90 degrees.

In some embodiments, the connector includes a first engagement member having first and second ribs defined by at least one recess in a bottom surface of the connector that is disposed adjacent the exterior surface of the battery housing. In some embodiments, the at least one recess includes three recesses. In some embodiments, the battery housing includes the second engagement member and the at least one slot being defined by at least two protrusions extending from the exterior surface of the battery housing. In some embodiments, the at least one slot includes two slots, and the at least two protrusions includes three protrusions arranged to define the at least two slots. In some embodiments, the three protrusions include a common protrusion, which defines a side of two of the at least two slots.

In some embodiments, a method of manufacturing a battery assembly is provided. In some embodiments, the method comprises the step of providing a battery housing having an exterior surface with a feedthrough pin extending therefrom for carrying an electrical potential and providing a connector including at least one electrical terminal and having a feedthrough pin aperture for accepting the feedthrough pin. In some embodiments, the connector body has a first engagement member, and the exterior surface includes a second engagement member configured to engage the first engagement member in an interference fit, friction fit, pressure fit and/or press fit engagement. In some embodiments, the method includes the step of pressing the connector onto the battery housing to engage the first and second engagement members together in a press fit manner with the feedthrough pin extending into the feedthrough aperture of the electrical terminal. In some embodiments, the method includes the step of electrically connecting the feedthrough pin to the electrical terminal once the connector body is interference fit, friction fit, pressure fit and/or press fit into engagement with the second engagement member.

The features and advantages of the present disclosure will become apparent from the following description read in conjunction with the accompanying drawings. The present disclosure is considered to include all functional combinations of the above described features and corresponding descriptions contained herein, and all combinations of further features described herein, and is not limited to the particular structural embodiments shown in the figures as examples. The scope and spirit of the present disclosure is considered to include modifications as may be made by those skilled in the art having the benefit of the present disclosure which substitute, for elements presented in the claims, devices or members upon which the claim language reads or which are equivalent thereto, and which produce substantially the same results associated with those corresponding examples identified in this disclosure for purposes of the operation of this disclosure. Additionally, the scope and spirit of the present disclosure is intended to be defined by the scope of the claim language itself and equivalents thereto without incorporation of structural or functional limitations discussed in the specification which are not referred to in the claim language itself.

Additional features and advantages of various embodiments will be set forth in part in the description, and in part will be apparent from the description, or may be learned by practice of various embodiments. The advantages of various embodiments will be realized and attained by means of the elements and combinations particularly pointed out in the description and appended claims.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

As used in this specification and the appended claims, in some embodiments, the singular forms "a," "an," and "the," include plural referents unless expressly and unequivocally limited to one referent. Thus, for example, reference to "a boss" includes one, two, three or more bosses.

Negative limitations are implicit and optional in this disclosure. If two elements or steps are shown directly contacting, or directly leading one to the next, without intervening elements or steps, this disclosure is intended to relate the elements are optionally directly connected or contacting without intervening elements, and likewise that steps in a procedure shown without intervening steps or operations are intended to positively relate that the steps are optional ordered without intervening steps or procedure. However, such implicit relation of negative limitations is to be considered optional and are not to be interpreted as excluding embodiments with intervening elements or steps unless specifically so noted and claimed.

Reference will now be made in detail to various embodiments of the present disclosure, examples of which are illustrated in the accompanying drawings. While the embodiments of the present disclosure will be described in conjunction with the illustrated embodiments, it will be understood that they are not intended to limit the invention to those embodiments. On the contrary, the disclosure is intended to cover all alternatives, modifications, and equivalents, which may be included within the disclosure as defined by the appended claims.

Figure 1:
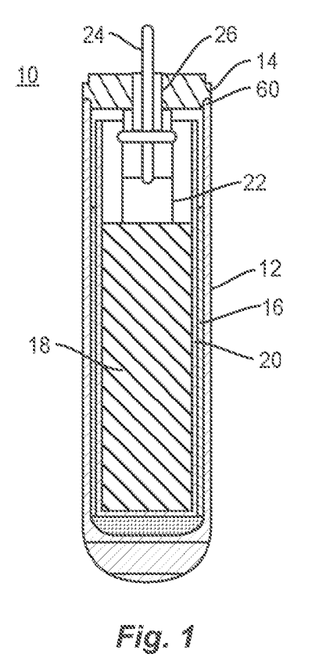
FIG. 1 is a cross-section view of components of one embodiment of a battery assembly.

Referring to FIG. 1, a battery assembly 10 for an implantable medical device (IMD) is shown. Battery assembly 10 includes a generally cylindrical battery housing 12 and a battery housing cover 14. Within battery housing 12 is an anode 16, a cathode 18 and a separator 20. Embedded within cathode 18 is current collector 22 which is connected to a feedthrough member or pin 24. Feedthrough pin 24 can be connected to, for example, an electronics assembly for an IMD. Battery assembly 10 provides that in operation, battery housing 12 and battery housing cover 14 have a negative potential, also known as "case negative" polarity. The outer surfaces of battery assembly 10 are designed to be exposed to bodily fluids.

In some embodiments, battery housing 12 and battery housing cover 14 are optionally made of an electrically conductive material such as alpha beta and beta titanium alloys such as Ti-6Al4V or Ti-I 5Mo, respectively, stainless steels, titanium, for example, grade 1, or any other grade. In some embodiments, anode 16 is optionally formed of lithium metal, cathode 18 is optionally formed of a hybrid mixture of carbon monofluoride (CFX) and silver vanadium oxide (CSVO) and may further contain carbon black or polytetrafluoroethylene (PTFE), or both and separator 20 is optionally formed of porous polypropylene film, such as that provided by Celgard, LLC of Charlotte, N.C. (e.g., CELGARD 2500, CELGARD 4560, and the like). In some embodiments, battery assembly 10 includes a liquid electrolyte (not shown) for facilitating ionic transport and forming a conductive pathway between anode 16 and cathode 18. In some embodiments, feedthrough pin 24 and current collector 22 are formed from an electrically conductive material such as, for example and not limitation, titanium, platinum, niobium, molybdenum, alloys of titanium, stainless steel, or alloys of any of these. In some embodiments, feedthrough pin 24 is a solid unitary component of a feedthrough in which the feedthrough pin is fixated in glass or ceramic (not shown) to be electrically insulated from battery housing 12 and hermetically sealed such that battery housing 12 contains the electrolyte in a leak proof manner. Other sealing methods including resin adhesives may be used. Feedthrough pin 24 passes aperture 26 to extend above battery housing cover 14 for engagement with a connector device, as described herein, or directly to an electronics assembly. In some embodiments, as discussed herein, in exemplary applications, feedthrough pin 24 is engaged with an electrical connector, such as, for example, a battery electrical connector (BEC), which provides a hot terminal connected to feedthrough pin 24 and a ground terminal connected to battery housing 12 via battery housing cover 14.

In some embodiments, battery housing cover 14 includes a divot or indentation 17 for identification on the exterior surface of battery housing cover 14 due to its relatively small size. For example, an outside diameter of battery housing 12 and battery housing cover 14 can range from about 2 mm to about 7.5 mm and can be any diameter between about 2 mm and about 7.5 mm. In some embodiments, the length of battery assembly 10 can range from about 8 mm to about 90 mm and can be any length between about 8 mm and about 90 mm. In some embodiments, for example, in an intra-heart IMD application, an outside diameter of battery housing 12 is in the lower end of the exemplary ranges presented above. See, for example, details of battery assembly construction, as provided in US Patent Application Publication No. US2013/0302665, published Nov. 14, 2013, which is hereby incorporated by reference herein for such disclosures.

Figure 2A:
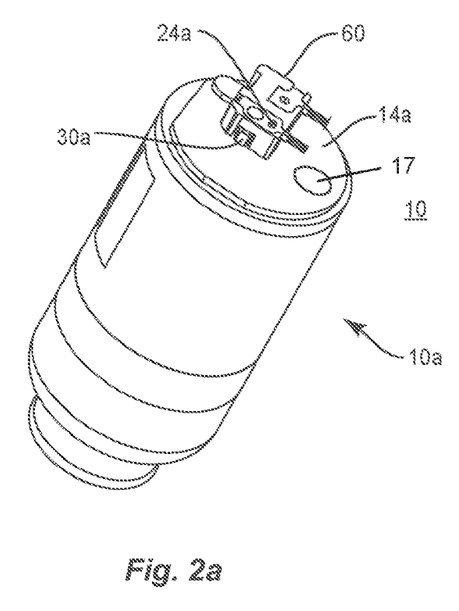
FIG. 2a is a perspective view of components of one embodiment of a battery assembly in accordance with the principles of the present disclosure.
Figure 2B:
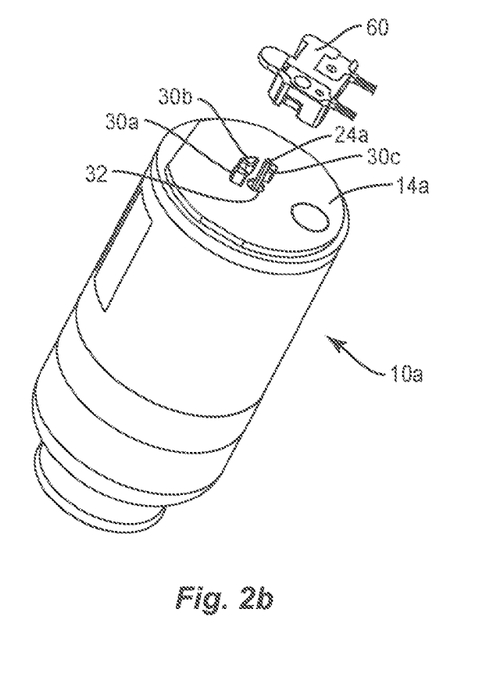
FIG. 2b is a perspective view of the components shown in FIG. 2a with parts separated.

In some embodiments, battery assembly 10 has a small size, such as, for example, small, miniature and/or microelectronic components. In some embodiments, battery assembly 10 has a small size and is assembled with a BEC (see FIG. 2a, for example), as described herein. In some embodiments, the BEC has an aperture for accepting feedthrough pin 24, which positions feedthrough pin 24 in contact with or proximately adjacent a hot terminal, as described herein, for the formation of an electrical connection therebetween by laser welding, soldering, or other electrical connection.

In some embodiments, a ground terminal tab (for example, ground terminal tab 40 shown in FIGS. 4a-4f) extends from the BEC to lay on battery housing cover 14 to permit electrical connection thereto via laser welding, soldering, or other electrical connection. In some embodiments, to effect the electrical connection, the BEC is placed in precise alignment with feedthrough pin 24 and battery housing cover 14 within error tolerances associated with alignment of an IMD electronics assembly and/or module (not shown) with battery assembly 10. In some embodiments, the IMD electronics assembly and/or module optionally seats on an annular lip of battery housing cover 14 so that terminals of the BEC are in precise alignment with battery housing cover 14 and when the IMD electronics assembly and/or module are seated, the hot and ground terminals of the BEC make electrical connection with corresponding contacts of the IMD electronics assembly and/or module. See, for example, a BEC connection to a battery assembly as provided in US Patent Application Publication No. US2007/0150020, published Jun. 28, 2007, which is hereby incorporated by reference for its disclosure of battery construction materials and techniques.

In one embodiment, as shown in FIGS. 2a-6, battery assembly 10, similar to that described herein, includes a battery housing 10a, similar to battery housing 12 described with regard to FIG. 1, assembled with a battery electrical connector (BEC) 60 mounted on a battery cover 14a, similar to battery housing cover 14 described with regard to FIG. 1. BEC 60 is seated on battery cover 14a such that feedthrough pin 24a extends through BEC 60.

To effect assembly of BEC 60 with battery cover 14a, one or more engagement members, such as, for example, bosses 30a-30c extend from a top surface of battery cover 14a and are positioned to matingly engage one or more engagement members of BEC 60, as described herein. Bosses 30a-30c matingly engage the engagement members of BEC 60 such that BEC 60 is guided and aligned into assembly with battery housing 10a, as described herein. In some embodiments, one or more of bosses 30a-30c can be wedge shaped. In some embodiments, bosses 30a-30c are spaced apart. In some embodiments, bosses 30a-30c have the same geometric configuration. In some embodiments, one or more of bosses 30a-30c have different geometric configurations.

Feedthrough pin 24a is passed through a feedthrough aperture 32 in battery cover 14a so as not to contact battery cover 14a. In some embodiments, feedthrough pin 24a is sealed in place by a sealing material. In some embodiments, the sealing material includes glass, resin, epoxy, or other sealant material that hermetically bonds feedthrough pin 24a to battery cover 14a and is biologically compatible with use in an IMD.

Referring to FIGS. 3d and 3e, and FIGS. 4a-4f, BEC 60 is aligned with battery cover 14a as facilitated by guided engagement of bosses 30a-30c with the engagement members of BEC 60 to facilitate assembly of BEC 60 with battery housing 10a. In some embodiments, bosses 30a-30c are positioned about feedthrough aperture 32 in a radial arrangement. In some embodiments, the radial arrangement facilitates machining of alignment bosses 30a-30c as feedthrough aperture 32 is centered in battery cover 14a.

In some embodiments, surfaces extending upward from battery cover 14a are referred to herein as "vertical" for purposes of identification, but may optionally taper inward with increasing distance from battery cover 14a to effect a mating engagement. In some embodiments, the mating engagement includes a mating engagement, mating configuration, mating contact, mating connection, mating attachment and/or assembly, as described herein. In some embodiments, the mating engagement of the engagement members, as described herein, includes an interference fit, friction fit, pressure fit, press fit and/or interlock that provides connection, attachment, mounting, contact, electrical connection or communication, relative positioning, alignment, guiding and/or locking of one or more components of battery assembly 10. In some embodiments, the mating engagement of the engagement members, as described herein, includes an engagement wherein one or more components of battery assembly 10 are engaged together by friction due to compression of at least one of the engagement members with or without an interlocking arrangement. In some embodiments, a press fit mating engagement may include a detent arrangement in combination with a press fit contact of surfaces.

Figure 3A:
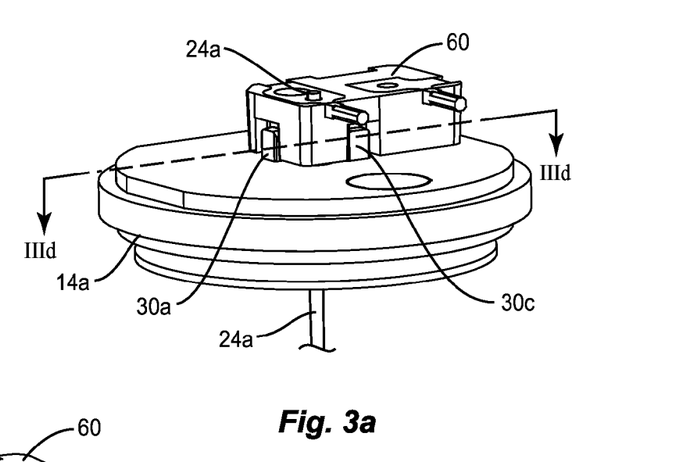
Figure 3B:
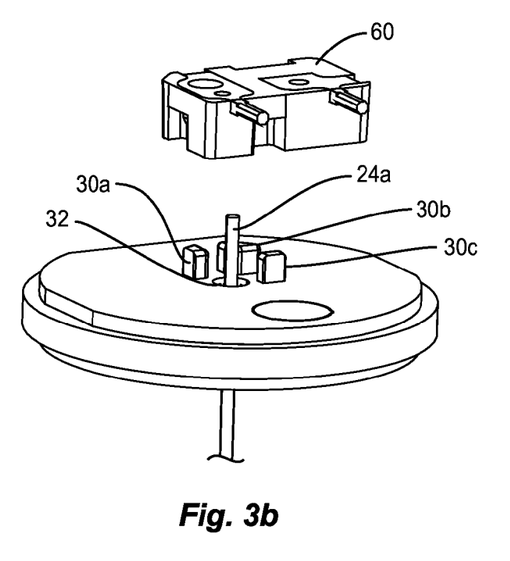
FIG. 3b is break away perspective view of components shown in FIG. 2a with parts separated.
Figure 3C:
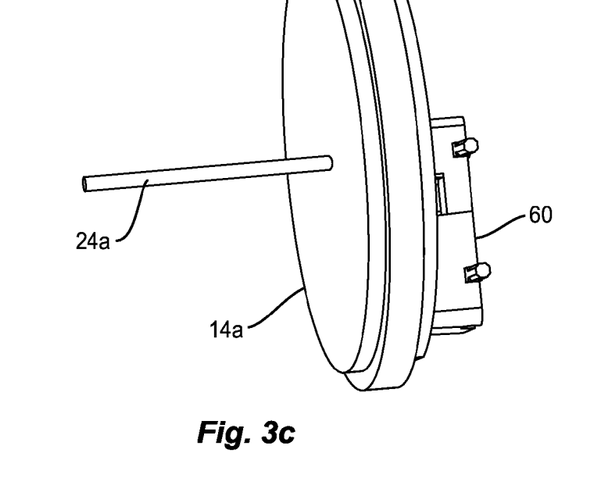
Figure 3D:
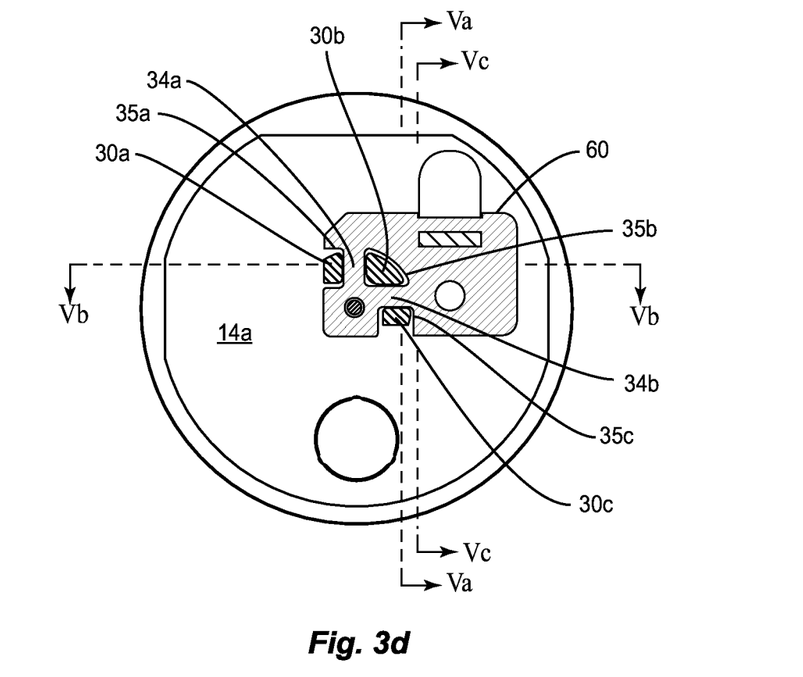
Figure 3E:
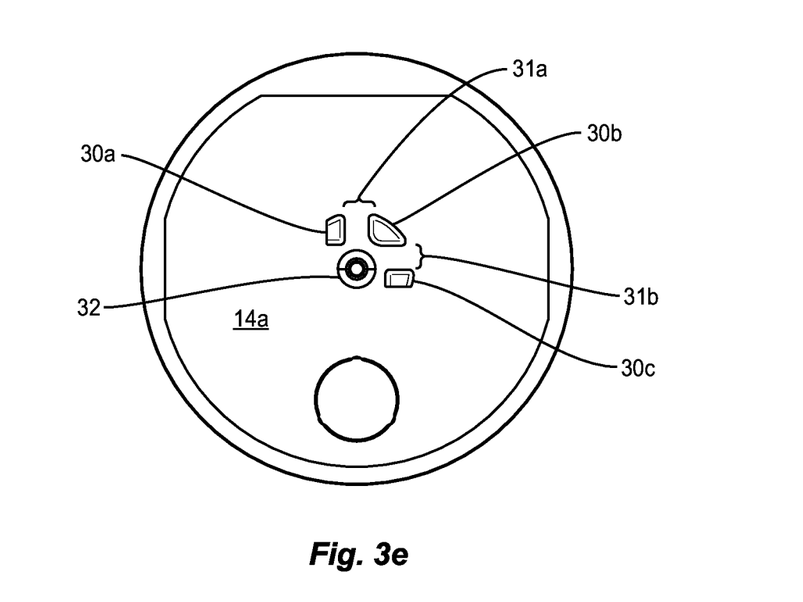
Figure 4A:
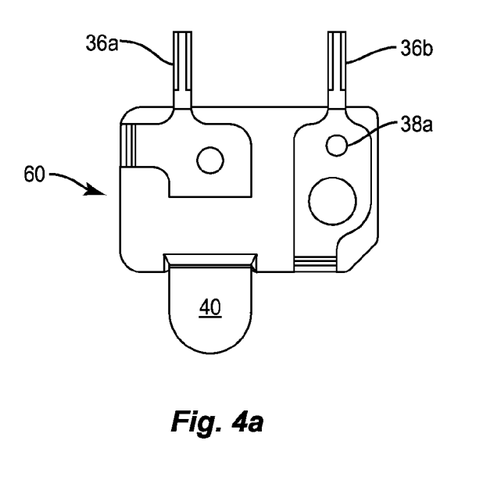
FIG. 4a is a plan view of components of one embodiment of a battery assembly in accordance with the principles of the present disclosure.
Figure 4B:
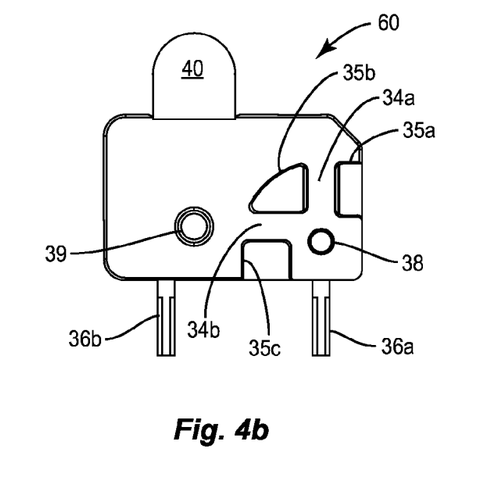
Figure 4C:
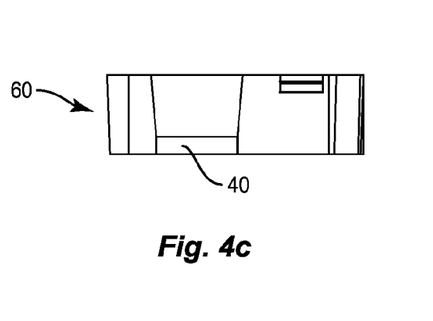
Figure 4D:
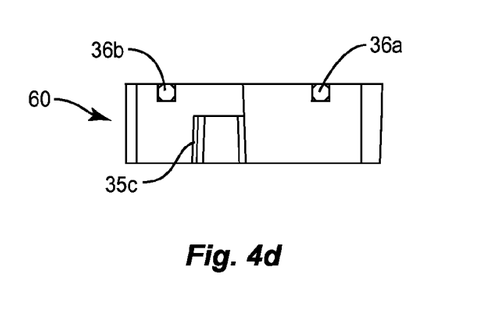
Figure 4E:
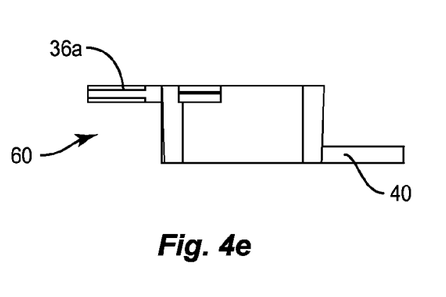
Figure 4F:
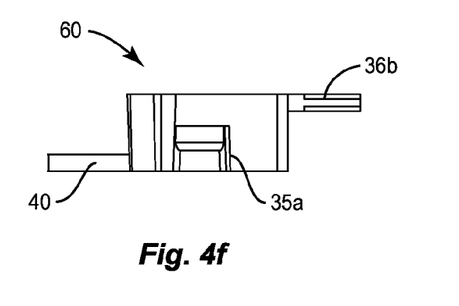

In some embodiments, bosses 30a-30c are radially distributed with battery cover 14a. In some embodiments, bosses 30a-30c are positioned in one or more configurations that are not radially centered about feedthrough aperture 32 and maintain distance tolerances with respect to feedthrough aperture 32. In some embodiments, bosses 30a-30c include surfaces having a selected radius of curvature. In some embodiments, battery cover 14a includes one or a plurality of bosses 30a-30c. In some embodiments, bosses 30a-30c include beveled edges to facilitate mating engagement with BEC 60. In some embodiments, bosses 30a-30c include outer surfaces milled to required tolerances for mating engagement with BEC 60.

In some embodiments, battery cover 14a includes cavities, such as, for example, slots 31a, 31b disposed adjacent bosses 30a-30c. The surfaces of bosses 30a-30c define slots 31a, 31b, which are configured for disposal of the engagement members of BEC 60 to facilitate assembly of BEC 60 with battery housing 10a.

In some embodiments, to effect assembly of BEC 60 with battery cover 14a, BEC 60 includes one or more engagement members, such as, for example, ribs 34a, 34b and the surfaces that define cavities, such as, for example, recesses 35a-35c. Ribs 34a, 34b and the surfaces that define recesses 35a-35c extend from a surface of BEC 60 and are positioned to matingly engage bosses 30a-30c. Recesses 35a-35c are configured for disposal of bosses 30a-30c.

Ribs 34a, 34b and the surfaces that define recesses 35a-35c matingly engage bosses 30a-30c. As ribs 34a, 34b and the surfaces that define recesses 35a-35c engage bosses 30a-30c, the engagement of the surfaces includes a guided alignment of the components such that BEC 60 is guided and aligned into assembly with battery housing 10a, as described herein. In some embodiments, the engagement of ribs 34a, 34b and the surfaces that define recesses 35a-35c with bosses 30a-30c includes a self-aligning and/or self-guided configuration. In some embodiments, BEC 60 is positioned in a vertical direction by engagement of a top surface of battery cover 14a but may be positioned by a limiting member or by insertion of BEC 60 to a predetermined position and retained by the mating engagement.

In some embodiments, ribs 34a, 34b are disposed with slots 31a, 31b in a guided alignment to position BEC 60 on battery cover 14a. In some embodiments, battery cover 14a includes slots 31a, 31b disposed adjacent bosses 30a-30c in an orthogonal arrangement. In some embodiments, battery cover 14a includes slots 31a, 31b disposed adjacent bosses 30a-30c in an orthogonal arrangement to facilitate positive positioning in both x and y directions in a plane of a top surface of battery cover 14a. In some embodiments, battery cover 14a includes slots 31a, 31b disposed adjacent bosses 30a-30c in a circular engagement.

Figure 5A:
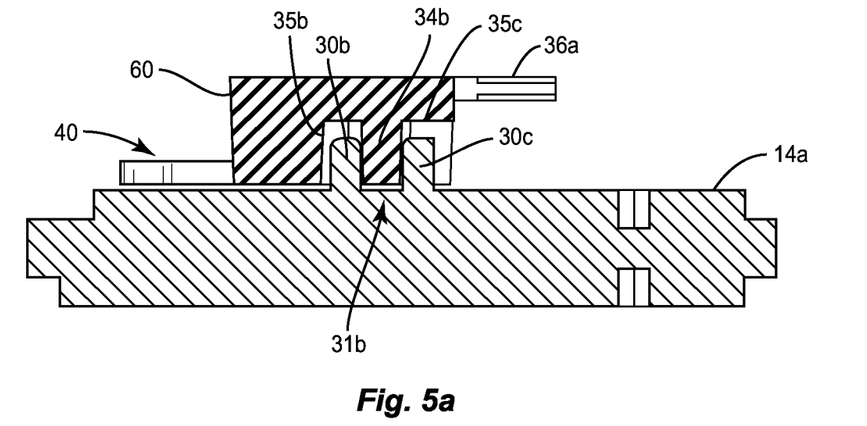
FIG. 5a is a side, cross section view of the components shown in FIG. 2a taken along line Va-Va of FIG. 3d.
Figure 5B:
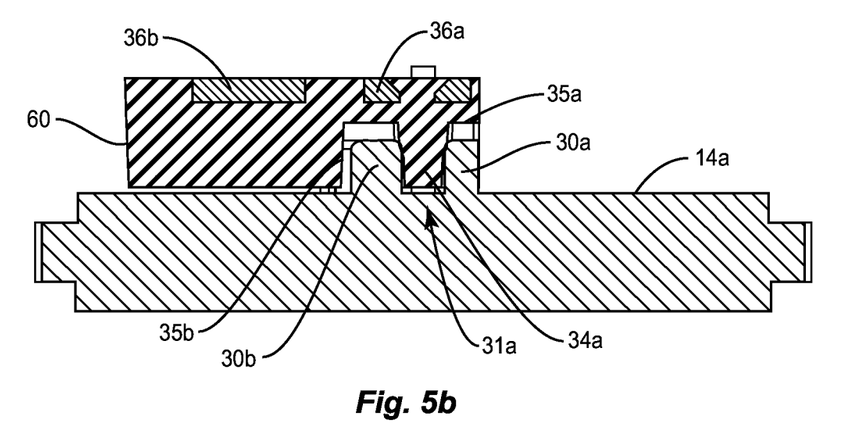
FIG. 5b is a side, cross section view of the components shown in FIG. 2a taken along line Vb-Vb of FIG. 3d.
Figure 5C:
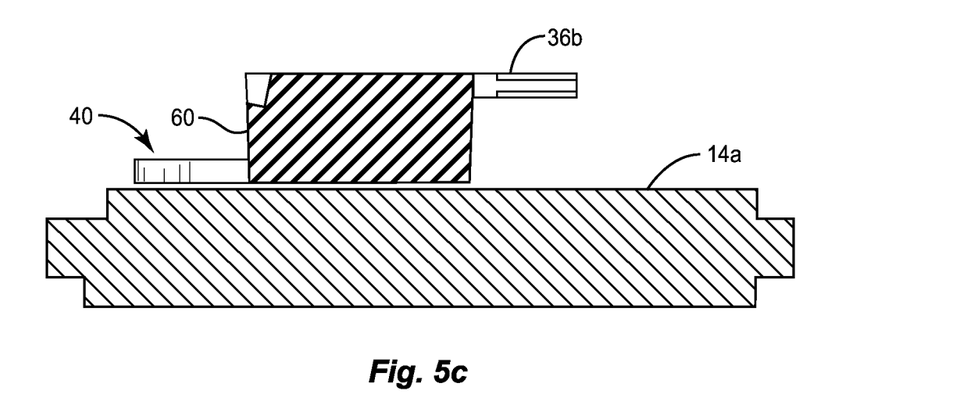
FIG. 5c is a side, cross section view of the components shown in FIG. 2a taken along line Vc-Vc of FIG. 3d.
Figure 6:
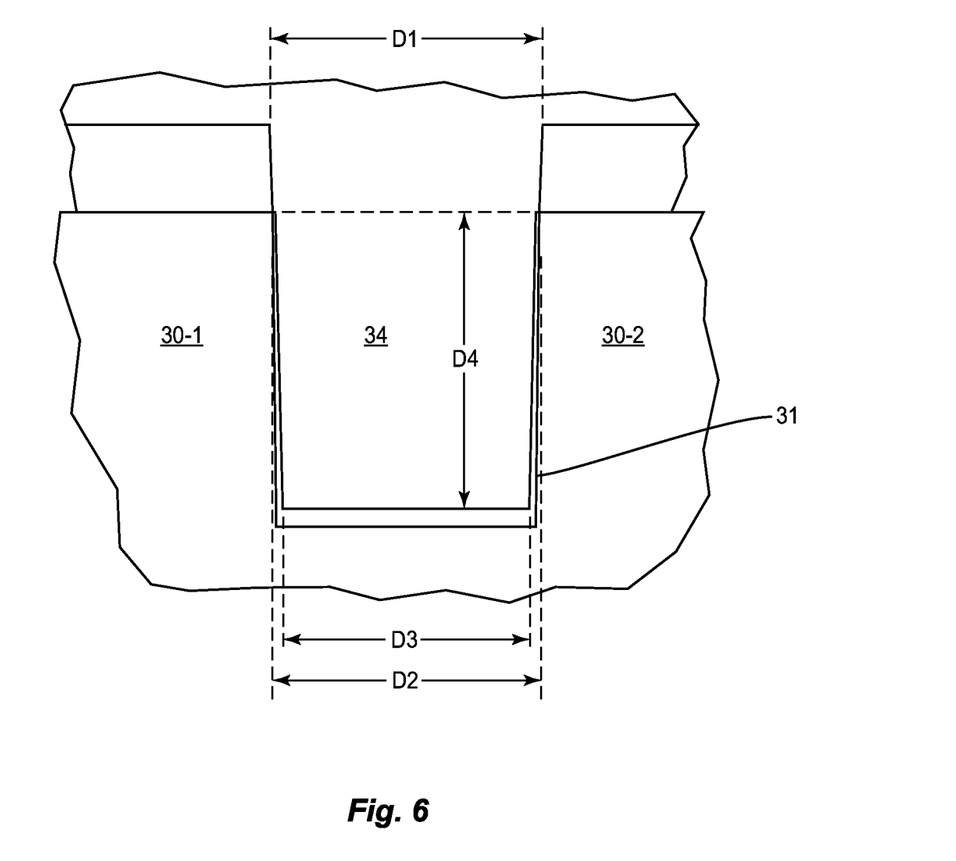

Bosses 30a-30c are disposed with recesses 35a-35c and ribs 34a, 34b are disposed with slots 31a, 31b such that bosses 30a-30c matingly engage ribs 34a, 34b and the surfaces that define recesses 35a-35c, as shown in FIGS. 5a-5c. Engagement of bosses 30a-30c with ribs 34a, 34b and the surfaces that define recesses 35a-35c includes a guided alignment of the components such that BEC 60 is guided and aligned into assembly with battery housing 10a. In some embodiments, for example, as shown in FIG. 6, rib 34 has a width D1 adjacent an end surface thereof, which is greater than a width D2 of slot 31 adjacent an end surface that defines its opening such that compressing of rib 34 and deflection of representative bosses 30-1 and 30-2 is effected. The width difference in dimensions D1 And D2 defines an interference fit, friction fit, pressure fit and/or press fit amount of the engagement. The height D4 of rib 34 in conjunction with the width difference of D1 and D3 defines a taper angle of rib 34. The engagement members of battery cover 14a matingly engage the engagement members of BEC 60 such that BEC 60 is guided and aligned into assembly with battery housing 10a.

In some embodiments, the engagement members of BEC 60 and/or battery cover 14a may be variously shaped, such as, for example, oval, oblong, triangular, square, polygonal, irregular, uniform, non-uniform, offset, staggered, undulating, arcuate, variable and/or tapered. In some embodiments, one or more of the engagement members may have various cross section configurations, such as, for example, oval, oblong, triangular, rectangular, square, polygonal, irregular, uniform, non-uniform, variable, tubular and/or tapered. In some embodiments, the engagement members of BEC 60 and/or battery cover 14a may be monolithic, integrally connected, connected, attached and/or adhered. In some embodiments, the engagement members of BEC 60 and/or battery cover 14a may include threads, mutual grooves, screws, adhesive, nails, barbs, raised elements, spikes, clips, snaps, friction fittings, compressive fittings, expanding rivets, staples, fixation plates, key/keyslot, tongue in groove, dovetail, magnetic connection and/or posts. In some embodiments, the engagement members of BEC 60 and/or battery cover 14a may be relatively disposed or arranged in a side by side, irregular, uniform, non-uniform, offset and/or staggered orientation or arrangement. In some embodiments, the cavities of BEC 60 and/or battery cover 14a may be variously shaped, such as, for example, oval, oblong, triangular, square, polygonal, irregular, uniform, non-uniform, offset, staggered, undulating, arcuate, variable and/or tapered.

In some embodiments, BEC 60 has terminals 36a, 36b embedded in BEC 60 during molding, as shown in FIGS. 5a-5c. In some embodiments, terminal 36a is a ground terminal, which makes electrical contact with battery cover 14a via laser welding. In some embodiments, terminal 36b is a "hot" terminal and is electrically connected to feedthrough pin 24a by laser welding and extends through terminal aperture 38a after extending through BEC feedthrough aperture 38. Alternative electrical connection techniques may be employed such as, for example, soldering or conductive epoxies or adhesives.

The terms "ground" and "hot" used herein are intended merely to convey a relative electrical potential between terminals 36a, 36b, and are not intended to convey any particular polarity, with the common usage of "ground" when discussing batteries generally referring to the case potential. While one feedthrough pin is shown for the present example, this disclosure is not limited by this example, and multiple feedthrough pins may be employed for applications requiring differing electrical potentials between terminals. Additionally, while battery housing 10a provides the ground potential, this is exemplary and not a requirement as a battery cover 14a may be formed of a non-conductive material with dual feedthrough pins employed to provide electrical power.

In some embodiments, recesses 35a-35c are molded into BEC 60. In some embodiments, recesses 35a-35c taper inward with increasing penetration into BEC 60, which permits release of a mold and simultaneously defines a tapered configuration of ribs 34a and 34b to facilitate mating engagement and guided alignment of ribs 34a, 34b in slots 31a, 31b.

Figure 7:
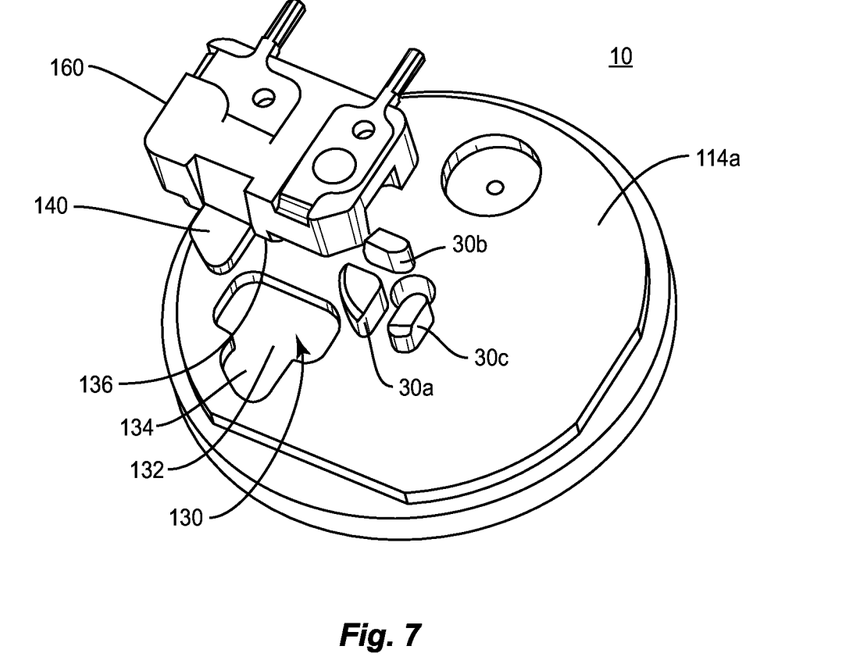
FIG. 7 is a perspective view of components of one embodiment of a battery assembly in accordance with the principles of the present disclosure with parts separated.

In one embodiment, as shown in FIG. 7, battery assembly 10, similar to that described herein, includes battery housing 10a, described herein with regard to FIGS. 2a-6, which comprises a battery cover 114a, similar to battery cover 14a described herein. Battery cover 114a includes bosses 30a-30c, as described herein, and an engagement member, similar to those described herein, such as, for example, the surfaces of battery cover 114a that define a recess 130. Recess 130 includes a portion 132 having five linear sides and being substantially rectangular, and a portion 134 having four linear sides and a substantially trapezoidal configuration.

Battery assembly 10 comprises a BEC 160, similar to BEC 60 described herein, which includes ribs 34a, 34b and the surfaces that define recesses 35a-35c, as described herein, and engagement members, similar to those described herein, such as, for example, a boss 136 and a ground tab 140, similar to the ground tabs described herein. Boss 136 and ground tab 140 extend from a surface of BEC 160 and are positioned to matingly engage portions 132, 134 of recess 130. Portions 132, 134 are configured for disposal of boss 136 and ground tab 140, respectively. Engagement of boss 136 and ground tab 140 with the surfaces that define portions 132, 134 includes a guided alignment of the components such that BEC 160 is guided and aligned into assembly with battery housing 10a, similar to that described herein. The engagement members of battery cover 114a matingly engage the engagement members of BEC 160 such that BEC 160 is guided and aligned into assembly with battery housing 10a.

In some embodiments, positioning of ground tab 140 and/or boss 136 radially outward from a feedthrough member, as described herein, prevents rotation of BEC 160 and excessive stress on laser welds and/or other connections of the components of battery housing 10a.

Figure 8A:
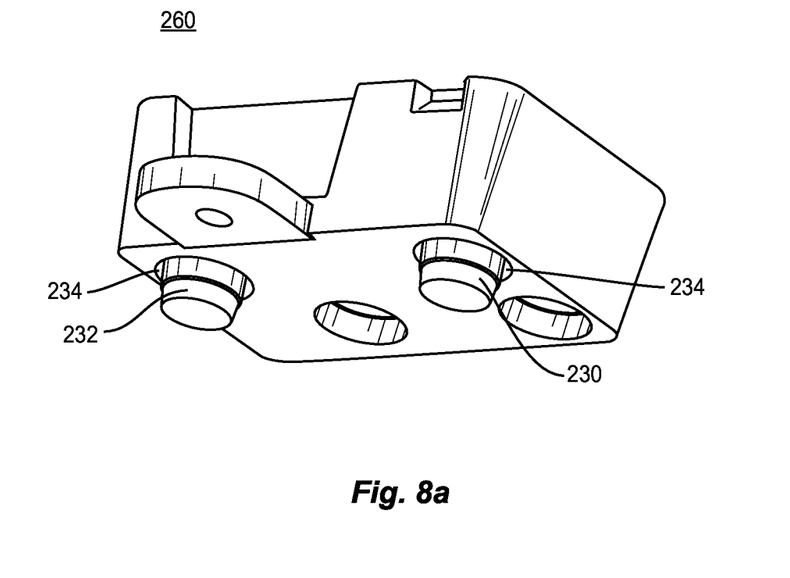
FIG. 8a is a perspective view of components of one embodiment of a battery assembly in accordance with the principles of the present disclosure.

In one embodiment, as shown in FIG. 8a, battery assembly 10, similar to that described herein, includes battery housing 10a, described herein with regard to FIGS. 2a-6, which comprises a battery cover (not shown), similar to the battery covers described herein. Battery assembly 10 comprises a BEC 260, similar to the BECs described herein, mounted on the battery cover. BEC 260 is seated on the battery cover such that a feedthrough member (not shown), similar to the feedthrough members described herein, extends through BEC 260. BEC 260 includes engagement members, similar to those described herein, such as, for example, cylindrical posts 230, 232. Posts 230, 232 extend from a surface of BEC 260 and each define a circumferential recess 234 thereabout.

To effect assembly of BEC 260 with the battery cover, one or more engagement members, as described herein, extend from a top surface of the battery cover and are positioned to matingly engage posts 230, 232, similar to that described herein. Engagement of posts 230, 232 and the engagement members of the battery cover includes a guided alignment of the components such that BEC 260 is guided and aligned into assembly with battery housing 10a, similar to that described herein.

Figure 8B:
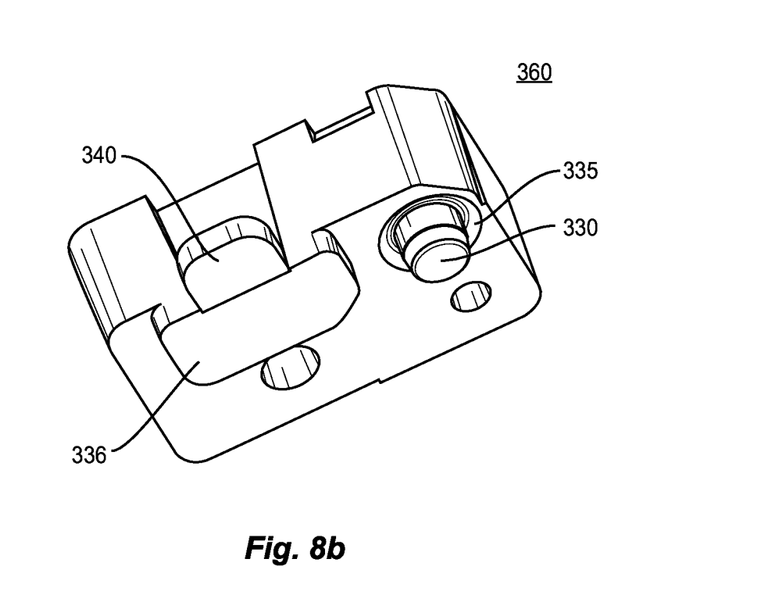
FIG. 8b is a perspective view of components of one embodiment of a battery assembly in accordance with the principles of the present disclosure.

In one embodiment, as shown in FIG. 8b, battery assembly 10, similar to that described herein, includes battery housing 10a, described herein with regard to FIGS. 2a-6, which comprises a battery cover (not shown), similar to the battery covers described herein. Battery assembly 10 comprises a BEC 360, similar to the BECs described herein, mounted on the battery cover. BEC 360 is seated on the battery cover such that a feedthrough member (not shown), similar to the feedthrough members described herein, extends through BEC 360.

BEC 360 includes engagement members, similar to those described herein, such as, for example, a boss 336 and a ground tab 340, similar to the ground tabs described herein, and a cylindrical post 330. Boss 336 has five linear sides and is substantially rectangular. Post 330 extends from a surface of BEC 360 and defines a circumferential recess 335 thereabout.

To effect assembly of BEC 360 with the battery cover, one or more engagement members, as described herein, extend from a top surface of the battery cover and are positioned to matingly engage boss 336, a ground tab 340 and cylindrical post 330, similar to that described herein. Engagement of boss 336, ground tab 340 and cylindrical post 330 and the engagement members of the battery cover includes a guided alignment of the components such that BEC 360 is guided and aligned into assembly with battery housing 10a, similar to that described herein.

Figure 9:
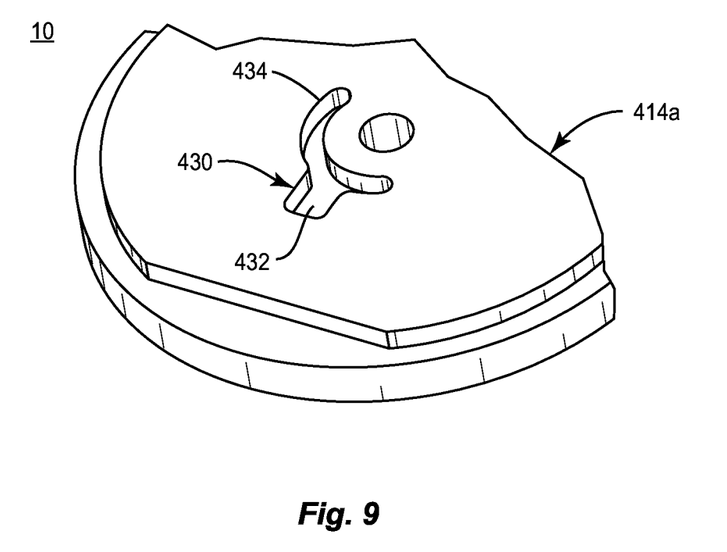
FIG. 9 is a break away perspective view of components of one embodiment of a battery assembly in accordance with the principles of the present disclosure.

In one embodiment, as shown in FIG. 9, battery assembly 10, similar to that described herein, includes battery housing 10a, as described herein, which comprises a battery cover 414a, similar to the battery covers described herein. Battery cover 414a includes an engagement member, similar to those described herein, such as, for example, the surfaces of battery cover 414a that define a recess 430. Recess 430 includes a linear portion 432 and an arcuate portion 434.

Battery assembly 10 comprises a BEC (not shown), similar to the BECs described herein, which includes engagement members, similar to those described herein. The engagement members of the BEC extend from a surface of the BEC and are positioned to matingly engage portions 432, 434 of recess 430. Portions 432, 434 are configured for disposal of the engagement members of the BEC. Engagement of the engagement members of the BEC with the surfaces that define portions 432, 434 includes a guided alignment of the components such that the BEC is guided and aligned into assembly with battery housing 10a, similar to that described herein. Portions 432, 434 matingly engage the engagement members of the BEC such that the BEC is guided and aligned into assembly with battery housing 10a.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A battery assembly comprising:
    a battery housing comprising an inner surface defining an opening, the battery housing including an outer surface and a plurality of bosses extending from the outer surface, the bosses being spaced apart from one another and the opening;
    a feedthrough member being disposed through the opening and extending from the battery housing; and
    a connector including at least one electrical terminal electrically contacting the feedthrough member, the connector including a plurality of spaced apart recesses, the recesses each being configured for disposal of one of the bosses to physically assemble the battery housing and the connector in a manner that prevents rotation of the connector relative to the battery housing.

2. A battery assembly according to claim 1, wherein the recesses are each configured for disposal of one of the bosses to align components of the battery assembly.

3. A battery assembly according to claim 1, wherein the recesses are each configured for disposal of one of the bosses to align the connector with the feedthrough member.

4. A battery assembly according to claim 1, wherein the recesses are each configured for disposal of one of the bosses to prevent axial translation of the connector relative to the battery housing.

5. A battery assembly according to claim 1, wherein the recesses are each configured for disposal of one of the bosses to prevent translation of the connector relative to the battery housing in a plurality of axial directions.

6. A battery assembly according to claim 1, wherein at least one of the bosses is wedge shaped.

7. A battery assembly according to claim 1, wherein one or more of the bosses have different geometric configurations.

8. A battery assembly according to claim 1, wherein the connector includes a grounding tab configured to permit electrical connection to the battery housing.

9. A battery assembly according to claim 1, wherein at least one of the recesses is tapered.

10. A battery assembly according to claim 1, wherein the bosses are each self-aligning with one of the recesses.

11. A battery assembly according to claim 1, wherein the bosses are circumferentially disposed about the opening.

12. A battery assembly according to claim 1, wherein the battery assembly comprises micro-electronic components.

13. A battery assembly according to claim 1, wherein the bosses each have the same geometric configuration.

14. A battery assembly according to claim 1, wherein the opening is centered in the battery housing.

15. A battery assembly according to claim 1, wherein surfaces of the connector that define the recesses engage the bosses in a mating configuration.

16. A battery assembly according to claim 1, wherein the recesses are molded into the connector.

17. A battery assembly according to claim 1, wherein the recesses each taper inward with increasing penetration into the connector.

18. A battery assembly according to claim 1, wherein the feedthrough pin is configured to be positioned within an aperture of the connector when the bosses are disposed in the recesses.

19. A battery assembly for use with a implantable medical device, the battery assembly comprising:

a battery housing comprising an anode and a cathode, the cathode being connected to a feedthrough pin that is configured to be connected to the implantable medical device, the battery housing comprising a battery cover having a top surface that defines an aperture, the feedthrough pin extending through the aperture, the battery cover including plurality of bosses extending from the top surface, the bosses being spaced apart from one another and the aperture; and a connector that engages the feedthrough pin, the connector including a plurality of spaced apart recesses, the recesses each being configured for disposal of one of the bosses to physically assemble the battery housing and the connector in a manner that prevents rotation of the connector relative to the battery housing.

20. A battery assembly comprising:

an implantable medical device;

a battery housing comprising an anode and a cathode, the cathode being connected to a feedthrough pin that is configured to be connected to the implantable medical device, the battery housing comprising a battery cover having a top surface that defines an aperture, the feedthrough pin extending through the aperture, the battery cover including plurality of bosses extending from the top surface, the bosses being spaced apart from one another and the aperture; and a connector that engages the feedthrough pin, the connector including a plurality of spaced apart recesses, the recesses each being configured for disposal of one of the bosses to physically assemble the battery housing and the connector in a manner that prevents rotation of the connector relative to the battery housing.

* * * * *